United States Patent
Namba et al.

(10) Patent No.: US 7,321,032 B2
(45) Date of Patent: Jan. 22, 2008

(54) METHOD OF DETECTING BIFIDOBACTERIUM INFANTIS

(75) Inventors: Kazuyoshi Namba, Zama (JP); Michiko Hatano, Zama (JP); Tomoko Yaeshima, Zama (JP); Norio Ishibashi, Zama (JP); Yoshitaka Tamura, Zama (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 160 days.

(21) Appl. No.: 10/543,491

(22) PCT Filed: Aug. 12, 2004

(86) PCT No.: PCT/JP2004/011609

§ 371 (c)(1),
(2), (4) Date: Jul. 26, 2005

(87) PCT Pub. No.: WO2005/080563

PCT Pub. Date: Sep. 1, 2005

(65) Prior Publication Data

US 2006/0281084 A1 Dec. 14, 2006

(30) Foreign Application Priority Data

Feb. 24, 2004 (JP) ............... 2004-047720

(51) Int. Cl.
*C07H 21/04* (2006.01)
*C12P 19/34* (2006.01)
*G01N 31/22* (2006.01)

(52) U.S. Cl. ............... 536/24.33; 435/91.2; 422/61
(58) Field of Classification Search ............... None
See application file for complete search history.

(56) References Cited

U.S. PATENT DOCUMENTS 5,443,951 A * 8/1995 Yamamoto et al. ............ 435/6

FOREIGN PATENT DOCUMENTS

| EP | 0 826 778 A1 * | 4/1998 |
| JP | 06-197763 | 7/1994 |
| JP | 11-123093 | 5/1999 |
| WO | WO 2005/039319 A2 * | 5/2005 |

OTHER PUBLICATIONS

Miyake et al., "Phylogenetic Analysis of the Genus *Bifidobacterium* and Related Genera Based on 16S rDNA Sequences," Microbiol. Immunol., 1998, vol. 42, No. 10, pp. 661-667 and associated Accession No. D86184 sequence listing.*
Buck et al., "Design Strategies and Performance of Custom DNA Sequencing Primers," Biotechniques, Sep. 1999, vol. 27, No. 3, pp. 528-536.*
Germond, et al. "Species Specific Identification of Nine Human *Bifidobacterium* spp. in Feces," *System. Appl. Microbiol.*, vol. 25, pp. 536-543, 2002.
Bergey's Manual of Systematic Bacteriology, vol. 2, Peter H.A. Sneath, Editor, pp. 1418-1434, Williams & Wilkins, Publisher, Baltimore, MD, 1986.
Gutell, et al. Comparative Anatomy of 16-S-like Ribosomal RNA, *Progress in Nucleic Acid Research and Molecular Biology*, vol. 32, pp. 155-216, 1985.
Brigidi, et al. "Specific Detection of *Bifidobacterium* Strains in a Pharmaceutical Probiotic Product and in Human Feces by Polymerase Chain Reaction," *Systematic and Applied Microbiology*, vol. 23, No. 3, pp. 391-399, Oct. 2000.
Leblond-Bourget, et al. "16S rRNA and 16S to 23S Internal Transcribed Spacer Sequence Analyses Reveal Inter- and Intraspecific *Bifidobacterium* Phylogeny," *International Journal of Systematic Bacteriology*, vol. 46, No. 1, pp. 102-111, Jan. 1996.
Matsuki, et al. "Distribution of Bifidobacterial Species in Human Intestinal Microflora Examined with 16S rRNA-Gene-Targeted Species-Specific Primers," *Applied and Environmental Microbiology*, vol. 65, No. 10, pp. 4506-4512, Oct. 1999.
Matsuki, et al. "Quantitative PCR with 16S rRNA-Gene-Targeted Species-Specific Primers for Analysis of Human Intestinal Bifidobacteria," *Applied and Environmental Microbiology*, vol. 70, No. 1, pp. 167-173, Jan. 2004.
Roy, et al. "Differentiation of Bifidobacteria by Use of Pulsed-Field Gel Electrophoresis and Polymerase Chain Reaction," *International Journal of Food Microbiology*, vol. 29, No. 1, pp. 11-29, 1996.
Wasilewska, et al. "Isolation and Identification of Bifidobacteria from Infant Gut," *Polish Journal of Food and Nutrition Sciences*, vol. 12, No. SI 1, pp. 90-94, 2003.

* cited by examiner

*Primary Examiner*—Kenneth R. Horlick
*Assistant Examiner*—Molly Baughman
(74) *Attorney, Agent, or Firm*—Knobbe, Martens, Olson & Bear, LLP

(57) ABSTRACT

PCR primers for detecting *Bifidobacterium infantis* comprising: a pair of a first oligonucleotide having a sequence of 20 or more continuous nucleotides selected from a nucleotide sequence of SEQ ID NO: 1 and a second oligonucleotide having a nucleotide sequence of SEQ ID NO: 2 or a nucleotide sequence of SEQ ID NO: 2 in which 0 to 7 nucleotides has been deleted from its 5'-terminal side is used to perform PCR using a chromosomal DNA or 16S rRNA of test bacteria as a template, and whether an amplicon of *Bifidobacterium infantis* is present or not is determined.

6 Claims, 1 Drawing Sheet

| | |
|---|---|
| 5'-tATCGGGGAGCAAGCGTGAGTGAGTTTACCCGTTGAATAAGCACcgg-3' | (SEQ ID NO: 1) |
| TATCGGGGAGCAAGCGTGA | (SEQ ID NO: 3) |
| TATCGGGGAGCAAGCGTGAG | (SEQ ID NO: 4) |
| ATCGGGGAGCAAGCGTGAGT | (SEQ ID NO: 5) |
| TCGGGGAGCAAGCGTGAGTG | (SEQ ID NO: 6) |
| CGGGGAGCAAGCGTGAGTGA | (SEQ ID NO: 7) |
| GGGGAGCAAGCGTGAGTGAG | (SEQ ID NO: 8) |
| GGGAGCAAGCGTGAGTGAGT | (SEQ ID NO: 9) |
| GGAGCAAGCGTGAGTGAGTT | (SEQ ID NO: 10) |
| GAGCAAGCGTGAGTGAGTTT | (SEQ ID NO: 11) |
| AGCAAGCGTGAGTGAGTTTA | (SEQ ID NO: 12) |
| GCAAGCGTGAGTGAGTTTAC | (SEQ ID NO: 13) |
| CAAGCGTGAGTGAGTTTACC | (SEQ ID NO: 14) |
| AAGCGTGAGTGAGTTTACCC | (SEQ ID NO: 15) |
| AGCGTGAGTGAGTTTACCCG | (SEQ ID NO: 16) |
| GCGTGAGTGAGTTTACCCGT | (SEQ ID NO: 17) |
| CGTGAGTGAGTTTACCCGTT | (SEQ ID NO: 18) |
| GTGAGTGAGTTTACCCGTTG | (SEQ ID NO: 19) |
| TGAGTGAGTTTACCCGTTGA | (SEQ ID NO: 20) |
| GAGTGAGTTTACCCGTTGAA | (SEQ ID NO: 21) |
| AGTGAGTTTACCCGTTGAAT | (SEQ ID NO: 22) |
| GTGAGTTTACCCGTTGAATA | (SEQ ID NO: 23) |
| TGAGTTTACCCGTTGAATAA | (SEQ ID NO: 24) |
| GAGTTTACCCGTTGAATAAG | (SEQ ID NO: 25) |
| AGTTTACCCGTTGAATAAGC | (SEQ ID NO: 26) |
| GTTTACCCGTTGAATAAGCA | (SEQ ID NO: 27) |
| TTTACCCGTTGAATAAGCAC | (SEQ ID NO: 28) |
| TTACCCGTTGAATAAGCACC | (SEQ ID NO: 29) |
| TACCCGTTGAATAAGCACCG | (SEQ ID NO: 30) |
| ACCCGTTGAATAAGCACCGG | (SEQ ID NO: 31) |

B

| | |
|---|---|
| 5'-GAACCCGCCCCGAAGGGAAACCCCA | (SEQ ID NO: 2) |
| CGAAGGGAAACCCCA | (SEQ ID NO: 32) |
| CGCCCCGAAGGGAAACCCCA | (SEQ ID NO: 33) |

US 7,321,032 B2

METHOD OF DETECTING BIFIDOBACTERIUM INFANTIS

This application is the U.S. National Phase under 35 U.S.C. §371 of International Application PCT/JP2004/011609, filed Aug. 12, 2004, which was published in a non-English language, which claims priority of Japanese Application No. 2004-047720, filed Feb. 24, 2004.

TECHNICAL FIELD

The present invention relates to a technique for detecting *Bifidobacterium infantis*. In particular, the present invention relates to primers for detecting *Bifidobacterium infantis* by PCR, and to a method and kit for detecting *Bifidobacterium infantis* using the primers. The present invention is useful in the field of microbial industry or the like.

BACKGROUND ART

In a breast-fed infant, bifidobacteria (bacteria of genus *Bifidobacterium*) accounts for 80 to 90% of intestinal bacterial flora, and is most predominant. Bifidobacteria is known to maintain the intestinal tract function of an infant and in the intestinal tract to prevent infections of putrefactive bacteria invading from the outside and opportunistic infection due to amplification of indigenous bacteria which usually exist in the intestinal tract and are harmless but become putrefactive when the infant is in a poor physical condition. In the field of the infant nutrition, it has been designed to prevent an infective disease or to promote treatment of an allergic disease by adding infant-type bifidobacteria to an infant formula or administering formulated bifidobacteria. For such use, from a physiological viewpoint, bifidobacteria existing in a human body is preferably administered to a human being, and human-type bifidobacteria is desirably used. Examples of known bifidobacteria existing in infant feces include *Bifidobacterium infantis* and *Bifidobacterium breve*. Of those, *Bifidobacterium infantis* is bifidobacteria detected only in an infant.

In order to evaluate the efficiency of such bifidobacteria application, for example, it is necessary to calculate the existing population of bifidobacteria in feces, and moreover, to judge a clinical effect by determining the individual species of *Bifidobacterium*. Accordingly, a technique for detecting *Bifidobacterium infantis* with reliability has been required.

Conventionally, bifidobacteria in feces or environmental substances has been identified by culturing a specimen under an aerobic condition, isolating colonies and performing a morphological test such as gram staining, observation of the shape of bacteria by microscopic examination or a biochemical test such as the determination of fructose-6-phosphate phosphoketolase activity, oxygen tolerance, or fermentation pattern of carbohydrate. The aforementioned specimen is cultured according to a standard method that is generally used for measurement of viable count or identification of bacterial species, but this approach has many problems. For example, not all bifidobacteria in feces can always be cultured. Moreover, the culture is time-consuming and troublesome because bifidobacteria must be cultured by using an anaerobic apparatus, and the culture requires about a few days to a week. Furthermore, bifidobacteria in a specimen must be stored anaerobically and at a low temperature and be subjected to analysis in the condition of viable cells, and much skill was required for the analysis.

On the other hand, recently, for identifying bifidobacteria, the similarity with a reference strain has been determined by the DNA-DNA homology test or by analysis of a nucleotide sequence of 16S rRNA gene. The DNA-DNA homology test is a method including culturing isolated bacteria to be tested, preparing the chromosomal DNA of the bacteria, and comparing it with that of a reference strain for homology by hybridization (Non-Patent Document 1). In order to prepare chromosomal DNA necessary for the test, the absolute requirement for the method is that the bacteria should be culturable. In addition, even if the bacteria are culturable, the method is troublesome because the chromosomal DNA must be prepared in large quantities. Furthermore, the method has, for example, an essential problem in that the method is suitable for examination of bacteria that have a far genetic distance from each other, but it is not sensitive for determining that of related species.

16S rRNA gene generally exists in prokaryotes, and there are nucleotide sequences conserved in different genus of bacteria and sequences conserved in different species of bacteria, so that it can be used for identification of bacterial species. The method can be performed by determining the nucleotide sequence of 16S rRNA gene of test bacteria, aligning the nucleotide sequence with a sequence of 16S rRNA gene of related species of bacteria (alignment), and analyzing the difference of the nucleotide sequences. However, the method needs to determine, as a reference, the sequence of 16S rRNA gene of bacteria existing in soil, sludge, feces, foods, or the like, and to analyze many sequences systematically, so that the method is time-consuming and troublesome (Non-Patent Document 2).

Moreover, use of a probe for detecting a specific sequence of 16S rRNA gene allows one to determine whether or not the test bacteria are the same bacteria as reference bacteria of which 16S rRNA gene has a known specific sequence. As an example of applying such a technique, a detection method using an oligonucleotide and derivatives thereof as probes for detecting 16S rRNA gene of *Bifidobacterium infantis* as a target is disclosed (Patent Document 1). However, it is a problem that the method is time-consuming. On the other hand, a technique in which bifidobacteria is analyzed using PCR primers capable of detecting 16S rRNA gene is known (Patent Document 2 and Non-Patent Document 3). However, the primers that are disclosed in those documents as specific primers for *Bifidobacterium infantis* have a problem of detecting *Bifidobacterium breve* in error.

Patent Document 1: JP 06-197763 A
Patent Document 2: JP 11-123093 A
Non-Patent Document 1: Bergey's Manual of Systematic Bacteriology Vol. 2 p1418-1434 (1986)
Non-Patent Document 2: Progress in Nucleic Acid Research and
Molecular Biology Vol. 32 p155-216 (1985)
Non-Patent Document 3: Systematic and Applied Microbiology Vol. 25 p. 536 (2002)

DISCLOSURE OF THE INVENTION

An object of the present invention is to provide: a PCR primer for amplifying 16S rRNA gene, which is specific for *Bifidobacterium infantis* without cross-reacting with other species of *Bifidobacterium*, and can detect *Bifidobacterium infantis* rapidly and simply; and a detection method using the primer.

To attain the aforementioned object, the inventors of the present invention have made extensive studies. As a result, they have found a PCR primer that can specifically detect *Bifidobacterium infantis*, and thereby, have accomplished the present invention.

That is, the present invention is as follows.

(1) PCR primers for detecting *Bifidobacterium infantis* consisting of a pair of: a first oligonucleotide having a sequence of 20 or more continuous nucleotides selected from a nucleotide sequence of SEQ ID NO: 1; and a second oligonucleotide having a nucleotide sequence of SEQ ID NO: 2 or a nucleotide sequence of SEQ ID NO: 2 in which 0 to 7 nucleotides have been deleted from its 5'-terminal side.

(2) The aforementioned PCR primer, wherein the first oligonucleotide has a nucleotide sequence selected from SEQ ID NOS: 5 to 28, and the second oligonucleotide has a nucleotide sequence selected from SEQ ID NO: 2, 32, or 33.

(3) A kit for detecting *Bifidobacterium infantis* including the aforementioned PCR primer.

(4) A method of detecting *Bifidobacterium infantis*, comprising: performing PCR using the aforementioned PCR primer and chromosomal DNA or 16S rRNA of test bacteria as a template; and determining whether an amplicon is present or not.

BRIEF DESCRIPTION OF THE DRAWING

[FIG. 1] This drawing shows a relationship of the PCR primers of the present invention. A and B represent a forward primer and a reverse primer, respectively.

DETAILED DESCRIPTION OF THE PREFERRED EMBODIMENTS

Hereinafter, the present invention will be described in detail.

The PCR primer of the present invention includes a pair of two kinds of oligonucleotides capable of amplifying 16S rRNA or 16S rRNA gene of *Bifidobacterium infantis* by PCR (polymerase chain reaction, White, T. J. et al., Trends Genet., 5, 185 (1989)). Of the aforementioned oligonucleotides, one is a first oligonucleotide having a sequence of 20 to 25 continuous nucleotides, preferably 20 continuous nucleotides selected from the nucleotide sequence of SEQ ID NO: 1, and the other is a second oligonucleotide having a nucleotide sequence of SEQ ID NO: 2 or a nucleotide sequence of SEQ ID NO: 2 in which 0 to 7 nucleotides, preferably 5 nucleotides have been deleted from 5'-terminal side.

Examples of the aforementioned first oligonucleotide include an oligonucleotide having a nucleotide sequence selected from SEQ ID NOS: 5 to 28. On the other hand, examples of the aforementioned second oligonucleotide include an oligonucleotide having a nucleotide sequence of SEQ ID NO: 2, 32, or 33.

The primer of the present invention can be synthesized according to a general DNA synthesis method that is well known to a person skilled in the art, for example, by using a DNA synthesizer. The primer of the present invention can also be obtained by ordering a DNA synthesis service.

*Bifidobacterium infantis* can be detected by performing PCR using the PCR primer of the present invention and a chromosomal DNA or 16S rRNA of test bacteria as a template, and determining whether an amplicon is present or not. That is, when a PCR amplification occurs specifically to the sequence of the primer, the region (targeted region) sandwiched between the sequences corresponding to the sequences of respective primers in the 16S rRNA gene of *Bifidobacterium infantis* is amplified. Accordingly, if the amplicons are obtained by using the PCR primer of the present invention, the test bacteria are identified to be *Bifidobacterium infantis*, or the test bacteria are considered to contain *Bifidobacterium infantis*. Moreover, the existing population of *Bifidobacterium infantis* can also be determined by performing PCR quantitatively. In the present invention, the detection of *Bifidobacterium infantis* includes: detecting whether *Bifidobacterium infantis* is present in a sample or not; in the case where test bacterium is a single species, identifying whether the test bacterium is *Bifidobacterium infantis* or not; and moreover, determining the existing population of *Bifidobacterium infantis* in the sample.

Test bacteria are not particularly limited as long as the bacteria are contained in a sample in which *Bifidobacterium infantis* may be present. Examples thereof include bacteria that are in feces, foods, or environmental substances such as soil. Preferably, the bacteria are *Bifidobacterium infantis* or bifidobacteria other than *Bifidobacterium infantis*. The test bacteria may be isolated single species of bacteria, or a mixture containing a plurality of species of bacteria.

The chromosomal DNA or 16S rRNA of the test bacteria is used as the aforementioned template. The preparation method of the chromosomal DNA or 16S rRNA is not particularly limited as long as those nucleic acids that may be used as PCR templates can be obtained. Generally, a method used in extraction or isolation of chromosomal DNA or RNA of bacteria can be adopted.

The bacterial cells used in extraction of the aforementioned nucleic acids can be obtained, for example, by culturing the aforementioned test bacteria obtained from feces, foods, soil, or the like anaerobically in the presence of carbon dioxide on a suitable medium such as a GAM medium to which 3% glucose is added. If necessary, the bacterial cells may be extracted from a medium by using water, a buffer, an organic solvent, or the like.

For extracting the target nucleic acid from the obtained bacterial cells, for example, commercial DNA extraction kits such as InstaGene Matrix (Japan Bio-Rad) and QIAamp DNA Stool Mini Kit (Qiagen) may be used. DNA may also be extracted by extracting DNA from cells according to a method described by Murmur (Journal of Molecular Biology Vol. 3 p208-218 (1961)), a benzyl chloride method (Nucleic Acid Research Vol. 21 p5279-5280 (1993)), or the like, and then removing RNA with ribonuclease. Before the extraction of nucleic acid, a substance for removing a PCR inhibitor such as bovine serum albumin is preferably added. On the other hand, RNA may be extracted according to a phenol method, a guanidine thiocyanate method, or the like. The DNA and RNA extraction methods are also described in Sambrook et al., "Molecular Cloning a Laboratory Manual, Second Edition", Cold Spring Harbor Laboratory Press (1989) and the like.

In the present invention, a PCR may be performed in a manner similar to general PCR using two kinds of oligonucleotide primers. Typically, denaturation, annealing, and an extension reaction are repeated for 20 to 35 cycles with incubating a reaction mixture containing template DNA, primers, and DNA polymerase at a temperature suitable for each reaction. In the case of using 16S rRNA as a template, a targeted region can be amplified by RT-PCR performed in combination with a reverse transcription reaction.

DNA polymerase used for PCR is not particularly limited as long as it can be used for the PCR. Examples thereof include: Taq DNA polymerase such as AmpliTaq Gold (Applied Biosystems), Takara Taq (TAKARA BIO INC.), and Platinum Taq DNA polymerase (Invitrogen); DNA polymerase such as Platinum Pfx DNA polymerase (Invitrogen) and Pyrobest DNA polymerase (TAKARA BIO INC.); and kits containing these enzymes and buffers.

The conditions of a PCR may be set appropriately in accordance with an enzyme to be used. Specific examples thereof include a condition of: incubating a reaction mixture at 94° C. for 10 minutes; repeating a reaction cycle consisting of denaturation (94° C., 30 seconds), annealing (55 to 65° C., 30 seconds), and extension (72° C., 30 seconds) for 30 cycles; and lastly, incubating the mixture at 72° C. for 10 minutes. The annealing temperature is preferably set to a Tm value of one primer having a Tm value lower than that of the other primer in a pair of primers. According to a nearest-neighbor method, when the Tm value is about 60° C., a preferable temperature is about 55° C., when the Tm value is about 65° C., a preferable temperature is about 60° C., and when the Tm value is about 70 to 75° C., a preferable temperature is about 65° C. As an amount ratio of template DNA and primers, the amount of the primers is preferably about 0.2 to 2 μmol per $10^2$ to $10^8$ copies of chromosomal DNA.

The presence or absence of the amplicon, or the amount of the amplicon obtained by a PCR can be determined according to a general detection or quantification method for a nucleic acid. For example, the amplicon can be detected by performing electrophoresis such as agarose gel electrophoresis or capillary electrophoresis and then staining the gel with ethidiumbromide or SYBRGreen I. Moreover, the amount of amplicon can be determined by fluorescence intensity, and the molecular weight thereof can be determined by comparison with a molecular weight marker. When electrophoresis is performed using an agarose gel in which a fluorescent dye is previously added, the amplicon can be detected without a staining process after the completion of electrophoresis. Furthermore, the presence or absence of the amplicon, or the amount of amplicon can also be confirmed by performing cycle sequencing of a PCR product and then determining the nucleotide sequence and length thereof using a DNA sequencer. In addition, according to a real time-PCR method, amplification can be detected continuously.

The PCR primers of the present invention may comprise a kit for detecting *Bifidobacterium infantis* alone or in combination with other components. Examples of the aforementioned other components include any one or more reagents necessary for extraction of nucleic acids, PCR, and detection of amplicons. The aforementioned kit may also include: as a positive control, a DNA fragment which has a part of a sequence of 16S rRNA gene of *Bifidobacterium infantis* and can be amplified by the PCR primer of the present invention; and/or, as a negative control, a DNA fragment which has a nucleotide sequence corresponding to that of the PCR primer of the present invention including mismatch of one or a few nucleotides.

As described above, the PCR primers of the present invention can be used for detecting *Bifidobacterium infantis*. Moreover, in the case of industrial production of bacterial cells of *Bifidobacterium infantis*, the measurement of viable count or monitoring of fermentation conditions can be easily performed by using the PCR primers of the present invention.

EXAMPLES

Hereinafter, the present invention will be illustrated in more detail by referring to examples, although the present invention is not limited to these examples.

<1>Synthesis of Primer

Oligonucleotides each having a nucleotide sequence shown in SEQ ID NO: 2 to 35 (referred to as Primers 2 to 35) were synthesized by means of a phosphoramidite method using a 3400 DNA synthesizer (manufactured by Applied Biosystems).

Primers 2, 5 to 28, 32, and 33 (SEQ ID NOS: 2, 5 to 28, 32, and 33) are the primers of the present invention (FIG. 1). Conveniently, Primers 5 to 28 are referred to as forward primers and Primers 2, 32, and 33 are referred as to reverse primers.

Primer 3 (SEQ ID NO: 3) is a PCR primer, produced by substituting a DNA sequence for an RNA probe for detecting 16S rRNA of *Bifidobacterium infantis* disclosed in JP 06-197763 A.

Primer 34 (SEQ ID NO: 34) and Primer 35 (SEQ ID NO: 35) are primers for specifically detecting *Bifidobacterium infantis* and disclosed in JP 11-123093 A as BiLONg and BiINF.

<2>Preparation of a Chromosomal DNA of Test Bacteria

Colonies of *Lactobacillus bifidus* were grown on a GAM agar medium (prepared by adding 3% (W/W) glucose in the commercial product (Nissui pharmaceutical Co., Ltd.)). Then, the colonies were collected using an inoculating needle, and they were suspended in a tube containing 1.0 ml of sterile water. The tube was centrifuged at 12,000 rpm for 1 minute, and the supernatant was removed. Two hundred micro liter of InstaGene Matrix™ (Japan Bio-Rad) was added to the resultant precipitate containing bacterial cells, and the mixture was incubated at 56° C. for 15 to 30 minutes. The resultant mixture was mixed with a Vortex Mixer for 10 seconds, and then incubated in boiling water for 8 minutes. The mixture was mixed with the Vortex Mixer for 10 seconds again, and centrifuged at 10,000 to 12,000 rpm for 2 minutes, thereby the supernatant was obtained. The DNA concentration was determined by measuring the absorbance of the supernatant liquid at a wavelength of 260 nm using a spectrophotometer. Subsequently, the supernatant was diluted with sterile water and thereby a 10 ng/μl of DNA solution was prepared.

The aforementioned bifidobacteria are as follows.
*Bifidobacterium infantis* (*B. infantis*) ATCC15697 strain
*Bifidobacterium breve* (*B. breve*) ATCC15700 strain
*Bifidobacterium bifidum* (*B. bifidum*) JCM1255 strain
*Bifidobacterium longum* (*B. longum*) JCM1217 strain
*Bifidobacterium pseudocatenulatum* (*B. pseudocatenulatum*) JCM1200 strain
*Bifidobacterium adolescentis* (*B. adolescentis*) JCM1275 strain
*Bifidobacterium dentium* (*B. dentium*) JCM1195 strain
*Bifidobacterium gallicum* (*B. gallicum*) JCM8224 strain
*Bifidobacterium angulatum* (*B. angulatum*) JCM7096 strain
*Bifidobacterium breve* (*B. breve*) JCM7020 strain Example 1

(1) PCR

The PCR reaction solution having the compositions described below was prepared, and PCR was performed under the following conditions using a PCR Thermal Cycler MR (Takara Shuzo Co., Ltd.). Incubating the solution at 94° C. for 10 minutes; repeating a reaction cycle consisting of denaturation (94° C., 30 seconds), annealing (65° C., 30 seconds), and extension (72° C., 30 seconds) for 30 cycles; and lastly, incubating it at 72° C. for 10 minutes. In Comparative Examples 1 and 2, annealing was performed at 55° C. for 30 seconds.

(PCR Reaction Solution Composition)

| | |
|---|---|
| Forward primer solution (10 μM) | 5 μl |
| Reverse primer solution (10 μM) | 5 μl |
| Sterile water | 53.5 μl |
| GeneAmp 10 × PCR Buffer II (Applied Biosystems) | 10 μl |
| 25 mM MgSO$_4$ | 6 μl |
| AmpliTaq Gold DNA polymerase (2.5 Unit) (Applied Biosystems) | 0.5 μl |
| GeneAmp dNTP MIX (2 mM of each of dATP, dTTP, dGTP, and dCTP) (Applied Biosystems) | 10 μl |
| DNA solution | 10 μl |

The combinations of forward primer and reverse primer are shown below.

[Table 1]

TABLE 1

| | Forward primer | Reverse primer |
|---|---|---|
| Example 1 | Primer 5 | Primer 33 |
| Comparative Example 1 | Primer 34 | Primer 35 |
| Comparative Example 2 | Primer 3 | Primer 33 |

(2) Detection of PCR Product

4 μl of a dye solution was added to 1 μl of a PCR solution, and electrophoresis was performed on 2% (w/w) of NuSieve 3:1 agarose (Cambrex Corporation) gel that had been prepared using 0.5×TBE buffer. The gel was stained with a SYBRGreenI (Cambrex Corporation) staining solution diluted to 20,000-fold using 0.5×TBE buffer. Subsequently, the fluorescence was observed at a wavelength of 300 nm using a densitometer AE-6920V-FX (ATTO Corporation). The amplicons were detected using a DNA marker. The results are shown in Table 2 and Table 3. In the tables, the symbol "+" represents that an amplicon was detected, and the symbol "−" represents that an amplicon was not detected.

[Table 2]

TABLE 2

| | presence or absence of an amplicon | |
|---|---|---|
| | Example 1 | Comparative Example 1 |
| B. infantis ATCC15697 | + | + |
| B. breve ATCC15700 | − | − |
| B. longum JCM1217 | − | − |
| B. bifidum JCM1255 | − | − |
| B. pseudocatenulatum JCM1200 | − | − |
| B. adolescentis JCM1275 | − | − |
| B. dentium JCM1195 | − | − |
| B. gallicum JCM8224 | − | − |
| B. angulatum JCM7096 | − | − |
| B. breve JCM7020 | − | + |

[Table 3]

TABLE 3

| | Comparative Example 2 |
|---|---|
| Strain Name | Presence or absence of an amplicon |
| B. infantis ATCC15697 | + |
| B. breve ATCC15700 | − |
| B. longum JCM1217 | − |
| B. bifidum JCM1255 | − |
| B. pseudocatenulatum JCM1200 | − |
| B. adolescentis JCM1275 | − |
| B. dentium JCM1195 | − |
| B. gallicum JCM8224 | − |
| B. angulatum JCM7096 | − |
| B. breve JCM7020 | + |

As shown in Table 2 and Table 3, the amplicons of both strains (*Bifidobacterium infantis* ATCC 15697 strain and *Bifidobacterium breve* JCM 7020 strain) were obtained in Comparative Example 1 and Comparative Example 2, so that *Bifidobacterium infantis* was not detected specifically. On the other hand, only amplicons of *Bifidobacterium infantis* ATCC 15697 strain having a length of 579 bp was obtained in Example 1.

Example 2

PCR were performed in a manner similar to that in Example 1, using Primers 4 to 31 as forward primers and Primer 33 as a reverse primer, and reaction products were detected. The results are shown in Table 4. The blank columns show that the experiment was not performed.

[Table 4]

TABLE 4

Presence or absence of an amplicon

| | Forward primer | | | | |
|---|---|---|---|---|---|
| | 4 | 5-28 | 29 | 30 | 31 |
| B. infantis ATCC15697 | + | + | + | + | + |
| B. breve ATCC15700 | − | − | − | − | + |
| B. longum JCM1217 | − | − | − | − | − |
| B. bifidum JCM1255 | − | − | − | − | − |
| B. pseudocatenulatum JCM1200 | + | − | − | − | − |
| B. adolescentis JCM1275 | − | − | − | − | − |
| B. dentium JCM1195 | − | − | − | − | − |
| B. gallicum JCM8224 | − | − | − | − | − |
| B. angulatum JCM7096 | − | − | − | + | + |

Example 3

PCR were performed in a manner similar to that in Example 2, and reaction products were detected. The annealing temperature in the reaction was 60° C.

[Table 5]

TABLE 5

Presence or absence of an amplicon

| | Forward primer | | | |
|---|---|---|---|---|
| | 5-28 | 29 | 30 | 31 |
| B. infantis ATCC15697 | + | + | + | + |
| B. breve ATCC15700 | − | − | + | + |
| B. longum JCM1217 | − | − | − | − |
| B. bifidum JCM1255 | − | − | − | − |
| B. pseudocatenulatum JCM1200 | − | − | − | − |
| B. adolescentis JCM1275 | − | − | + | + |
| B. dentium JCM1195 | − | − | − | − |
| B. gallicum JCM8224 | − | − | + | + |
| B. angulatum JCM7096 | − | + | + | + |

Example 4

PCR were performed in a manner similar to that in Example 1, using Primers 5, 16, and 28 as forward primers and Primer 32 as a reverse primer, and reaction products were detected. The annealing temperature in the reaction was 60° C. As a result, amplicons of *Bifidobacterium infantis* ATCC 15697 were obtained.

Example 5

PCR were performed in a manner similar to that in Example 1 using Primers 5, 16, and 28 as forward primers and Primer 33 as a reverse primer, and reaction products were detected. The annealing temperature in the reaction was 60° C. or 65° C. As a result, at both temperatures, amplicons of *Bifidobacterium infantis* ATCC 15697 were obtained.

Example 6

PCR were performed in a manner similar to that in Example 1 using Primers 5, 16, and 28 as forward primers and Primer 2 as a reverse primer, and reaction products were detected. The annealing temperature in the reaction was 60° C. As a result, amplicons of *Bifidobacterium infantis* ATCC 15697 were obtained.

Example 7

PCR were performed in a manner similar to that in Example 1 using Primers 5 and 16 as forward primers and Primer 2 as a reverse primer, and reaction products were detected. The annealing temperature in the reaction was 65° C. As a result, amplicons of *Bifidobacterium infantis* ATCC 15697 were obtained.

As described above, the primer of the present invention can detect *Bifidobacterium infantis* with extremely high specificity.

INDUSTRIAL APPLICABILITY

According to the present invention, *Bifidobacterium infantis* can be detected simply, rapidly, and without showing a cross-reaction with other species of bifidobacteria.

What is claimed is:

1. PCR primers for detecting *Bifidobacterium infantis* comprising:
   a first oligonucleotide consisting of a sequence of 20 or more continuous nucleotides selected from a nucleotide sequence of SEQ ID NO: 1; and
   a second oligonucleotide consisting of a nucleotide sequence of SEQ ID NO: 2 or a nucleotide sequence of SEQ ID NO: 2 in which 0 to 7 nucleotides have been deleted from its 5'-terminal side.

2. The PCR primers according to claim 1, wherein the first oligonucleotide has a nucleotide sequence selected from the group consisting of SEQ ID NOS: 5 to 28 and the second oligonucleotide has a nucleotide sequence selected from the group consisting of SEQ ID NO: 2, 32, or 33.

3. A kit for detecting *Bifidobacterium infantis* comprising the PCR primers according to claim 1.

4. A method of detecting *Bifidobacterium infantis* comprising:
   performing PCR using the PCR primers according to claim 1 and a chromosomal DNA or 16S rRNA of test bacteria as a template; and
   determining whether an amplicon is present or not.

5. A kit for detecting *Bifidobacterium infantis* comprising the PCR primers according to claim 2.

6. A method of detecting *Bifidobacterium infantis*, comprising:
   performing PCR using the PCR primers according to claim 2 and a chromosomal DNA or 16S rRNA of test bacteria as a template; and
   determining whether an amplicon is present or not.

* * * * *

SEQUENCE LISTING

<160> NUMBER OF SEQ ID NOS: 35

<210> SEQ ID NO 1
<211> LENGTH: 43
<212> TYPE: DNA
<213> ORGANISM: Artificial
<220> FEATURE:
<223> OTHER INFORMATION: an artificially synthesized primer sequence

<400> SEQUENCE: 1
atcggggagc aagcgtgagt gagtttaccc gttgaataag cac                43

<210> SEQ ID NO 2
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 2
gaacccgccc cgaagggaaa cccca                                    25

<210> SEQ ID NO 3
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 3
tatcggggag caagcgtga                                           19

<210> SEQ ID NO 4
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 4
tatcggggag caagcgtgag                                              20

<210> SEQ ID NO 5
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 5
atcggggagc aagcgtgagt                                              20

<210> SEQ ID NO 6
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 6
tcggggagca agcgtgagtg                                              20

<210> SEQ ID NO 7
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 7
cggggagcaa gcgtgagtga                                              20

<210> SEQ ID NO 8
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 8
ggggagcaag cgtgagtgag                                              20

<210> SEQ ID NO 9
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 9
gggagcaagc gtgagtgagt                                              20

<210> SEQ ID NO 10
<211> LENGTH: 20
<212> TYPE: DNA

```
<213> ORGANISM: Artificial
<220> FEATURE:
<223> OTHER INFORMATION: an artificially synthesized primer sequence

<400> SEQUENCE: 10
ggagcaagcg tgagtgagtt                                              20

<210> SEQ ID NO 11
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 11
gagcaagcgt gagtgagttt                                              20

<210> SEQ ID NO 12
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 12
agcaagcgtg agtgagttta                                              20

<210> SEQ ID NO 13
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 13
gcaagcgtga gtgagtttac                                              20

<210> SEQ ID NO 14
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 14
caagcgtgag tgagtttacc                                              20

<210> SEQ ID NO 15
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 15
aagcgtgagt gagtttaccc                                              20

<210> SEQ ID NO 16
<211> LENGTH: 20
<212> TYPE: DNA
<213> ORGANISM: Artificial
<220> FEATURE:
<223> OTHER INFORMATION: an artificially synthesized primer sequence
```

<400> SEQUENCE: 16
agcgtgagtg agtttacccg                                               20

<210> SEQ ID NO 17
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 17
gcgtgagtga gtttacccgt                                               20

<210> SEQ ID NO 18
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 18
cgtgagtgag tttacccgtt                                               20

<210> SEQ ID NO 19
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 19
gtgagtgagt ttacccgttg                                               20

<210> SEQ ID NO 20
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 20
tgagtgagtt tacccgttga                                               20

<210> SEQ ID NO 21
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 21
gagtgagttt acccgttgaa                                               20

<210> SEQ ID NO 22
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 22
agtgagttta cccgttgaat                                               20

<210> SEQ ID NO 23

```
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 23
gtgagtttac ccgttgaata                                              20

<210> SEQ ID NO 24
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 24
tgagtttacc cgttgaataa                                              20

<210> SEQ ID NO 25
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 25
gagtttaccc gttgaataag                                              20

<210> SEQ ID NO 26
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 26
agtttacccg ttgaataagc                                              20

<210> SEQ ID NO 27
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 27
gtttacccgt tgaataagca                                              20

<210> SEQ ID NO 28
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 28
tttacccgtt gaataagcac                                              20

<210> SEQ ID NO 29
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 29
```

-continued ttacccgttg aataagcacc                                        20

<210> SEQ ID NO 30
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 30
tacccgttga ataagcaccg                                        20

<210> SEQ ID NO 31
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 31
acccgttgaa taagcaccgg                                        20

<210> SEQ ID NO 32
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 32
ccccgaaggg aaacccca                                          18

<210> SEQ ID NO 33
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 33
cgccccgaag ggaaacccca                                        20

<210> SEQ ID NO 34
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 34
ttccagttga tcgcatggtc                                        20

<210> SEQ ID NO 35
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 35
ggaaacccca tctctgggat                                        20